(12) United States Patent
Abdel-Meguid et al.

(10) Patent No.: US 6,706,487 B1
(45) Date of Patent: Mar. 16, 2004

(54) MONOCLONAL ANTIBODY AND THE METHOD OF USING THE ANTIBODY

(75) Inventors: Sherin S. Abdel-Meguid, Exton, PA (US); Yen Sen Ho, Berwyn, PA (US); Stephen D. Holmes, Harlow (GB); Alexander H. Taylor, Exton, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/914,695

(22) PCT Filed: Mar. 17, 2000

(86) PCT No.: PCT/US00/07349

§ 371 (c)(1), (2), (4) Date: Aug. 31, 2001

(87) PCT Pub. No.: WO00/56771

PCT Pub. Date: Sep. 28, 2000

Related U.S. Application Data

(60) Provisional application No. 60/125,299, filed on Mar. 19, 1999.

(51) Int. Cl.[7] .................. G01N 33/53; C07K 16/00
(52) U.S. Cl. ............... 435/7.1; 435/7.23; 435/326; 435/335; 530/388.23; 530/387.1; 530/300; 530/326; 530/327; 530/328; 530/329; 530/330; 536/23.1
(58) Field of Search ............. 530/388.23, 388.1, 530/387.1; 435/326, 335, 346; 536/23.53

(56) References Cited

FOREIGN PATENT DOCUMENTS

| EP | 0 528 767 | 2/1993 |
|---|---|---|
| EP | 0 712 863 | 5/1996 |
| EP | 0 974 600 | 1/2000 |
| WO | WO 99/11237 | 6/1993 |
| WO | WO 99/09063 | 2/1999 |

OTHER PUBLICATIONS

Rekvig, et al., "Molecular Analyses of Anti–DNA Antibodies Induced by Polymavirus BK in Balb/c Mice". *Journal of Immunology*, 41(6):593–602 (1995).

Bonilla, et al., "V Kappa Gene Usage, Idiotype Expression and Antigen Binding Among Clones Expressing the VHX24 Gene Family Derived from Naïve and Anti–Idiotype Immune Balb/c Mice". *Journal of Immunology*, 145(2): 616–622 (1990).

Jones, et al., "Expression of TIMP3 mRNA in Elevated in Retinas Affected by Simplex Retinitis Pigmentosa". *FEBS Letters*, 352(2): 171–174 (1994).

Rosa et al. p619, a giant protein related to the chromosome condensation regulator RCC1, stimulates guanine nucleotide exchange on ARF1 and Rab proteins. 1996. EMBO J., 15(16): 4262–4273.*

Taniguchi, et al., "Characterization of anti–human interleukin–18 (IL–18)/interferon–gamma–inducing factor (IGIF) monoclonal antibodies and their application in the measurement of human IL–18 by ELISA," *Journal of Immunological Methods*, 206(1–2): 107–113 (1997).

Dinarello, et al., "Overview of Interleukin–18: More Then An Interferon–Gamma Inducing Factor," *Journal of Leukocyte Biology*, 63(6): 658–664 (1998).

* cited by examiner

*Primary Examiner*—Elizabeth Kemmerer
*Assistant Examiner*—Dong Jiang
(74) *Attorney, Agent, or Firm*—Elizabeth J. Hecht; Edward R. Gimmi; Charles M. Kinzig

(57) ABSTRACT

Chimeric, humanized and other IL-18 mAbs, derived from high affinity neutralizing mAbs, pharmaceutical compositions containing same, methods of treatment and diagnostics are provided.

8 Claims, 6 Drawing Sheets

Vk2c10

```
                   1 0                           30
 1   D    I    Q    M    T    Q    S    P    A    S    L    S    A    S    L     15
     GAC  ATT  CAA  ATG  ACC  CAG  TCT  CCA  GCT  TCC  CTG  TCT  GCA  TCT  CTG
     CTG  TAA  GTT  TAC  TGG  GTC  AGA  GGT  CGA  AGG  GAC  AGA  CGT  AGA  GAC
```

CDRI

```
         50                           7 0                              90
16   G    E    T    V    S    I    E    C   |L    A    S    E    D    I    Y|    30
     GGA  GAA  ACT  GTC  TCC  ATC  GAA  TGT |CTG  GCA  AGT  GAG  GAC  ATA  TAC|
     CCT  CTT  TGA  CAG  AGG  TAG  CTT  ACA |GAC  CGT  TCA  CTC  CTG  TAT  ATG|
```

```
                                  1 10                          13 0
31  |T    Y    L    T|   W    Y    Q    Q    K    P    G    K    S    P    Q     45
    |ACT  TAT  TTA  ACA|  TGG  TAT  CAG  CAG  AAA  CCA  GGG  AAA  TCT  CCT  CAA
    |TGA  ATA  AAT  TGT|  ACC  ATA  GTC  GTC  TTT  GGT  CCC  TTT  AGA  GGA  GTT
```

CDRII

```
                       150                         1 70
46   L    L    I    Y   |G    A    N    K    L    Q    D|   G    V    P    S     60
     CTC  CTG  ATC  TAT |GGT  GCA  AAT  AAG  TTG  CAA  GAT|  GGG  GTC  CCA  TCA
     GAG  GAC  TAG  ATA |CCA  CGT  TTA  TTC  AAC  GTT  CTA|  CCC  CAG  GGT  AGT
```

```
             19 0                           210
61   R    F    S    G    S    G    S    G    T    Q    Y    S    L    K    I     75
     CGG  TTC  AGT  GGC  AGT  GGA  TCT  GGC  ACA  CAG  TAT  TCT  CTC  AAG  ATC
     GCC  AAG  TCA  CCG  TCA  CCT  AGA  CCG  TGT  GTC  ATA  AGA  GAG  TTC  TAG
```

```
        2 30                          25 0                             270
76   S    G    I    Q    P    E    D    E    G    D    Y    F    C   |L    Q|    90
     AGC  GGC  ATA  CAA  CCT  GAA  GAT  GAA  GGG  GAT  TAT  TTC  TGT |CTA  CAG|
     TCG  CCG  TAT  GTT  GGA  CTT  CTA  CTT  CCC  CTA  ATA  AAG  ACA |GAT  GTC|
```

CDRIII

```
                                 2 90                           31 0
91  |G    S    K    F    P    L    T|   F    G    S    G    T    K    L    E     105
    |GGT  TCC  AAG  TTT  CCG  CTC  ACG|  TTC  GGT  TCT  GGG  ACC  AAG  CTG  GAG
    |CCA  AGG  TTC  AAA  GGC  GAG  TGC|  AAG  CCA  AGA  CCC  TGG  TTC  GAC  CTC
```

```
106  I    K    R    108
     ATC  AAA  CGG
     TAG  TTT  GCC
```

```
                1 0                           30
1    E   V   Q   L   Q   Q   S   G   A   E   L   V   R   P   G    15
     GAG GTC CAG CTA CAG CAG TCT GGG GCT GAG CTT GTG AGA CCT GGG
     CTC CAG GTC GAT GTC GTC AGA CCC CGA CTC GAA CAC TCT GGA CCC 50                          7 0                        90
16   T   S   V   K   L   S   C   K   V   S   G   E   I   S   T    30
     ACC TCT GTG AAG TTA TCT TGC AAA GTT TCT GGC GAA ATA AGT ACA
     TGG AGA CAC TTC AAT AGA ACG TTT CAA AGA CCG CTT TAT TCA TGT

CDRI
    ┌─────────────────┐                1 10                         13 0
31  │G   Y   Y   F   H│  F   V   R   R   R   P   G   Q   G   L    45
    │GGA TAC TAT TTC CAC│ TTT GTG AGG CGA AGG CCT GGA CAG GGT CTG
    │CCT ATG ATA AAG GTG│ AAA CAC TCC GCT TCC GGA CCT GTC CCA GAC
    └─────────────────┘
                                        CDRII
                           150                      ┌─1 70──────────────
46   E   W   I   G   R   I   D   P   E   D   D   S   T   K   Y    60
     GAA TGG ATA GGA AGG ATT GAT CCT GAG GAT GAT AGT ACT AAA TAT
     CTT ACC TAT CCT TCC TAA CTA GGA CTC CTA CTA TCA TGA TTT ATA 19 0                          210
61   A   E   R   F   K   D   R   A   T   L   T   A   Q   T   S    75
     GCT GAG AGG TTC AAA GAC│ AGG GCG ACG CTC ACT GCA CAA ACA TCC
     CGA CTC TCC AAG TTT CTG│ TCC CGC TGC GAG TGA CGT GTT TGT AGG
     ──────────────────────┘

2 30                         25 0                       270
76   S   N   T   A   Y   L   N   L   S   S   L   T   S   E   D    90
     TCC AAC ACA GCC TAC CTG AAC CTC AGC AGC CTG ACC TCT GAG GAC
     AGG TTG TGT CGG ATG GAC TTG GAG TCG TCG GAC TGG AGA CTC CTG 2 90                    31 0
91   T   A   T   Y   F   C   T   T   W   R   I   Y   R   D   S   105
     ACT GCA ACT TAT TTT TGT ACC ACA│TGG CGG ATA TAC CGA GAT AGT
     TGA CGT TGA ATA AAA ACA TGG TGT│ACC GCC TAT ATG GCT CTA TCA
                                    └──────────────────────────
     CDRIII
                   330                           3 50
106  S   G   R   P   F   Y   V   M   D   A   W   G   Q   G   A   120
     TCT GGC CGC CCC TTC TAT GTT ATG GAT GCC│TGG GGT CAA GGA GCT
     AGA CCG GCG GGG AAG ATA CAA TAC CTA CGG│ACC CCA GTT CCT CGA
     ──────────────────────────────────────┘

37 0
121  S   V   T   V   S   S       126
     TCA GTC ACT GTC TCC TCA
     AGT CAG TGA CAG AGG AGT
```

```
                 1 0                      30
 1   D   V   V   M   T   Q   T   P   L   S   L   P   V   S   L    15
     GAC GTT GTT ATG ACT CAA ACT CCT CTC TCC CTG CCT GTC AGT CTT
     CTG CAA CAA TAC TGA GTT TGA GGA GAG AGG GAC GGA CAG TCA GAA

CDR I
         50                          7 0                         90
16   G   D   Q   A   S   I   S   C  |R   S   S   Q   S   L   V|   30
     GGA GAT CAA GCC TCC ATC TCT TGC|AGA TCT AGT CAG AGC CTT GTA|
     CCT CTA GTT CGG AGG TAG AGA ACG|TCT AGA TCA GTC TCG GAA CAT|

1 10                   13 0
31  |H   S   N   G   N   T   Y   L   H|  W   Y   L   Q   K   P    45
    |CAC AGT AAT GGA AAC ACC TAT TTA CAT| TGG TAC CTG CAG AAG CCA
    |GTG TCA TTA CCT TTG TGG ATA AAT GTA| ACC ATG GAC GTC TTC GGT

CDR II
                     150                   1 70
46   G   Q   S   P   K   L   L   I   Y  |K   V   S   N   R   F|   60
     GGC CAG TCT CCA AAG CTC CTG ATC TAC|AAA GTT TCC AAC CGA TTT|
     CCG GTC AGA GGT TTC GAG GAC TAG ATG|TTT CAA AGG TTG GCT AAA|

19 0                   210
61  |S|  G   V   P   D   R   F   S   G   S   G   S   G   T   D    75
    |TCT| GGG GTC CCA GAC AGG TTC AGT GGC AGT GGA TCA GGT ACA GAT
    |AGA| CCC CAG GGT CTG TCC AAG TCA CCG TCA CCT AGT CCA TGT CTA 2 30                    25 0                    270
76   F   T   L   K   I   S   R   V   E   A   E   D   L   G   V    90
     TTC ACA CTC AAG ATC AGC AGA GTG GAG GCT GAG GAT CTG GGA GTT
     AAG TGT GAG TTC TAG TCG TCT CAC CTC CGA CTC CTA GAC CCT CAA

CDR III
                             2 90                     31 0
91   Y   F   C  |S   Q   S   T   H   V   P   P   Y   T|  F   G    105
     TAT TTC TGC|TCT CAA AGT ACA CAT GTT CCT CCG TAC ACG|TTC GGA
     ATA AAG ACG|AGA GTT TCA TGT GTA CAA GGA GGC ATG TGC|AAG CCT 330
106  G   G   T   K   L   E   I   K   R    114
     GGG GGG ACC AAG CTG GAA ATA AAA CGG
     CCC CCC TGG TTC GAC CTT TAT TTT GCC
```

```
                    10                         30
1    Q   V   T   L   K   E   S   G   P   G   I   L   K   P   S    15
     CAA GTT ACT CTT AAG GAG TCT GGC CCT GGG ATA TTG AAG CCC TCA
     GTT CAA TGA GAA TTC CTC AGA CCG GGA CCC TAT AAC TTC GGG AGT 50                     70                      90
16   Q   T   L   S   L   T   C   S   F   S   G   F   S   L   S    30
     CAG ACC CTC AGT CTG ACT TGT TCT TTC TCT GGG TTT TCT CTG AGC
     GTC TGG GAG TCA GAC TGA ACA AGA AAG AGA CCC AAA AGA GAC TCG 110                      130
31   | T   S   G   M   G   I   A | W   V   R   Q   P   S   G   K    45
     | ACT TCT GGT ATG GGT ATT GCC| TGG GTT CGT CAG CCT TCA GGG AAG
     | TGA AGA CCA TAC CCA TAA CGG| ACC CAA GCA GTC GGA AGT CCC TTC 150                         170
46   G   L   E   W   L   A  | D   I   W   W   D   D   N   K   Y |   60
     GGT CTG GAG TGG CTG GCA| GAC ATT TGG TGG GAT GAT AAT AAG TAT|
     CCA GAC CTC ACC GAC CGT| CTG TAA ACC ACC CTA CTA TTA TTC ATA|

190                          210
61   | Y   N   P   S   L   E   S | Q   L   T   I   S   K   D   T    75
     | TAT AAT CCA TCC CTG GAG AGC| CAG CTC ACA ATC TCC AAG GAT ACC
     | ATA TTA GGT AGG GAC CTC TCG| GTC GAG TGT TAG AGG TTC CTA TGG 230                     250                      270
76   S   R   N   Q   V   F   L   T   I   T   S   V   D   T   A    90
     TCC AGA AAC CAG GTA TTC CTC ACG ATC ACC AGT GTG GAC ACT GCA
     AGG TCT TTG GTC CAT AAG GAG TGC TAG TGG TCA CAC CTG TGA CGT 290                         310
91   D   S   A   T   Y   Y   C   A   R  | H   H   Y   D   G   S    105
     GAT TCT GCC ACT TAT TAC TGT GCT CGT| CAT CAT TAC GAC GGT AGT
     CTA AGA CGG TGA ATA ATG ACA CGA GCA| GTA GTA ATG CTG CCA TCA 330                        350
106  | S   L   L   P   M   D   Y | W   G   Q   G   T   S   V   T    120
     | AGC CTC CTG CCT ATG GAC TAC| TGG GGT CAA GGA ACC TCA GTC ACC
     | TCG GAG GAC GGA TAC CTG ATG| ACC CCA GTT CCT TGG AGT CAG TGG

121  V   S   S        123
     GTC TCC TCA
     CAG AGG AGT
```

```
                1 0                            30
 1    D    I    Q    M    T    Q    S    P    A    S    L    S    A    S    L    15
      GAT  ATT  CAA  ATG  ACG  CAG  TCT  CCA  GCT  TCC  CTG  TCT  GCA  TCT  CTG
      CTA  TAA  GTT  TAC  TGC  GTC  AGA  GGT  CGA  AGG  GAC  AGA  CGT  AGA  GAC 50                       7 0         CDR I                  90
 16   G    E    T    V    S    I    E    C   │L    A    S    E    D    I    Y│  30
      GGA  GAA  ACT  GTC  TCC  ATC  GAA  TGT │CTA  GCA  AGT  GAG  GAC  ATA  TAC│
      CCT  CTT  TGA  CAG  AGG  TAG  CTT  ACA │GAT  CGT  TCA  CTC  CTG  TAT  ATG│

1 10                      13 0
 31  │S    Y    L    A│   W    Y    Q    Q    K    P    G    K    S    P    Q    45
     │AGT  TAT  TTA  GCA│  TGG  TAT  CAA  CAG  AAG  CCA  GGG  AAA  TCT  CCT  CAG
     │TCA  ATA  AAT  CGT│  ACC  ATA  GTT  GTC  TTC  GGT  CCC  TTT  AGA  GGA  GTC

150       CDR II             1 70
 46   L    L    I    Y  │A    T    K    R    L    Q    D│  G    V    P    S    60
      CTC  CTG  ATC  TAT│GCC  ACA  AAA  AGG  TTG  CAA  GAT│GGG  GTC  CCA  TCA
      GAG  GAC  TAG  ATA│CGG  TGT  TTT  TCC  AAC  GTT  CTA│CCC  CAG  GGT  AGT 19 0                      210
 61   R    F    S    G    S    G    S    G    T    Q    Y    S    L    K    I    75
      CGG  TTC  AGT  GGC  AGT  GGA  TCT  GGC  ACA  CAG  TAT  TCT  CTC  AAA  ATA
      GCC  AAG  TCA  CCG  TCA  CCT  AGA  CCG  TGT  GTC  ATA  AGA  GAG  TTT  TAT 2 30                       25 0                            270
 76   S    D    M    Q    P    E    D    E    G    D    Y    F    C   │L    Q│   90
      AGC  GAC  ATG  CAA  CCT  GAA  GAT  GAA  GGG  GAT  TAT  TTC  TGT │CTA  CAG│
      TCG  CTG  TAC  GTT  GGA  CTT  CTA  CTT  CCC  CTA  ATA  AAG  ACA │GAT  GTC│

CDR III              2 90                                31 0
 91  │N    S    K    F    P    V    T│   F    G    S    G    T    K    L    E    105
     │AAT  TCC  AAG  TTT  CCG  GTC  ACG│  TTC  GGT  TCT  GGG  ACC  AAG  CTG  GAG
     │TTA  AGG  TTC  AAA  GGC  CAG  TGC│  AAG  CCA  AGA  CCC  TGG  TTC  GAC  CTC

106  I    K    R    108
      ATC  AAA  CGG
      TAG  TTT  GCC
```

```
                    10                          30
 1    E   V   Q   L   Q   Q   S   G   A   E   L   V   R   P   G   15
      GAG GTT CAG CTT CAG CAG TCT GGG GCT GAG CTT GTG AGA CCT GGG
      CTC CAA GTC GAA GTC GTC AGA CCC CGA CTC GAA CAC TCT GGA CCC 50                      70                      90
 16   T   S   V   K   F   S   C   K   V   S   G   D   T   P   T   30
      ACC TCT GTG AAG TTT TCT TGC AAA GTT TCT GGC GAT ACC CCT ACA
      TGG AGA CAC TTC AAA AGA ACG TTT CAA AGA CCG CTA TGG GGA TGT

CDR I               110                     130
 31   | T   Y   Y   V   H | F   V   R   Q   R   P   G   Q   G   L   45
      | ACA TAC TAC GTG CAC| TTT GTG AGA CAA AGG CCT GGA CAG GGT CTG
      | TGT ATG ATG CAC GTG| AAA CAC TCT GTT TCC GGA CCT GTC CCA GAC 150                    170    CDR II
 46   E   W   I   G  | R   I   D   P   E   D   T   S   T   K   Y |  60
      GAA TGG ATA GGA| AGG ATT GAT CCT GAG GAT ACT AGT ACT AAA TAT|
      CTT ACC TAT CCT| TCC TAA CTA GGA CTC CTA TGA TCA TGA TTT ATA|

190                     210
 61   | A   E   K   F   R   N | K   A   T   F   T   A   D   P   S   75
      | GCT GAG AAG TTC AGA AAT| AAG GCG ACA TTC ACT GCA GAT CCA TCC
      | CGA CTC TTC AAG TCT TTA| TTC CGC TGT AAG TGA CGT CTA GGT AGG 230                     250                     270
 76   S   N   T   A   Y   L   N   L   S   S   L   T   P   E   D   90
      TCC AAC ACA GCC TAC CTA AAC CTC AGC AGC CTG ACC CCT GAG GAC
      AGG TTG TGT CGG ATG GAT TTG GAG TCG TCG GAC TGG GGA CTC CTG 290                    310
 91   T   A   T   Y   F   C   T   I  | M   R   Y   H   S   T   Y  105
      ACT GCA ACC TAT TTT TGT ACC ATA| ATG CGG TAC CAT AGT ACC TAT
      TGA CGT TGG ATA AAA ACA TGG TAT| TAC GCC ATG GTA TCA TGG ATA

CDR III            330                  350
106   | R   V   Y   V   M   D   F | W   G   Q   G   T   A   V   T  120
      | AGG GTC TAT GTT ATG GAT TTC| TGG GGT CAA GGA ACT GCA GTC ACT
      | TCC CAG ATA CAA TAC CTA AAG| ACC CCA GTT CCT TGA CGT CAG TGA

121   V   S      122
      GTC TCC TC
      CAG AGG AG
```

FIGURE 6

MONOCLONAL ANTIBODY AND THE METHOD OF USING THE ANTIBODY

This application claims benefit of U.S. provisional application No. 60/125,299, filed on Mar. 19 1999.

FIELD OF THE INVENTION

The present invention relates generally to the field of antibodies and altered antibodies, useful in the treatment and diagnosis of conditions mediated by IL-18, and more specifically to mAbs, Fabs, chimeric and humanized antibodies.

BACKGROUND OF THE INVENTION

Human interleukin-18 is a recently identified cytokine that is synthesized as a biologically inactive 193 amino acid precursor protein (Ushio et al., *J. Immunol.* 156:4274, 1996). Cleavage of the precursor protein, for example by caspase-1 or caspase-4, liberates the 156 amino acid mature protein (Gu et al., *Science* 275:206, 1997; Ghayur et al., *Nature* 386:619, 1997), which exhibits biological activities that include the costimulation of T cell proliferation, the enhancement of NK cell cytotoxicity, the induction of IFN-γ production by T cells and NK cells, and the potentiation of T helper type 1 (Th1) differentiation (Okamura et al., *Nature* 378:88, 1995; Ushio et al., *J. Immunol.* 156:4274, 1996; Micallef et al., *Eur. J. Immunol.* 26:1647, 1996; Kohno et al., *J. Immunol.* 158:1541, 1997; Zhang et al., *Infect. Immunol.* 65:3594, 1997; Robinson et al., *Immunity* 7:571, 1997). In addition, IL-18 is an efficacious inducer of human monocyte proinflammatory mediators, including IL-8, tumor necrosis factor-α (TNF-α), and prostaglandin $E_2$ ($PGE_2$) (Ushio, S. et al., J. Immunol. 156:4274–4279, 1996; Puren, A. J. et al., J. Clin. Invest. 10:711–721, 1997; Podolin et al., *J. Immunol.* submitted, 1999).

The previously cloned IL-1 receptor-related protein (IL-1Rrp) (Parnet et al., *J. Biol. Chem.* 271:3967, 1996) was recently identified as a subunit of the IL-18 receptor (Kd=18 nM) (Torigoe et al., *J. Biol. Chem.* 272:25737, 1997). A second subunit of the IL-18 receptor exhibits homology to the IL-1 receptor accessory protein, and has been termed AcPL (for accessory protein-like). Expression of both IL-1 Rrp and AcPL are required for IL-18-induced NF-κB and JNK activation (Born et al., *J. Biol. Chem.* 273:29445, 1998). In addition to NF-κB and JNK, IL-18 signals through IL-1 receptor-associated kinase (IRAK), p56lck (LCK), and mitogen-activated protein kinase (MAPK) (Micallef et al., *Eur. J. Immunol.* 26:1647, 1996; Matsumoto et al., *Biophys Biochem. Res. Comm.* 234:454, 1997; Tsuji-Takayama et al., *Biochem. Biophys. Res. Comm.* 237:126, 1997).

Th1 cells, which produce proinflammatory cytokines such as IFN-γ, IL-2 and TNF-β (Mosmann et al., *J. Immunol.* 136:2348, 1986), have been implicated in mediating many of autoimmune diseases, including multiple sclerosis (MS), rheumatoid arthritis (RA), type 1, or insulin dependent, diabetes (IDDM), inflammatory bowel disease (IBD), and psoriasis (Mosmann and Sad, *Immunol. Today* 17:138, 1996). Thus, antagonism of a TH1-promoting cytokine such as IL-18 would be expected to inhibit disease development. Il-18 specific mAbs could be used as an antagonist.

The role of IL-18 in the development of autoimmune diseases has been demonstrated. Accordingly, it has been demonstrated that IL-18 expression is significantly increased in the pancreas and spleen of the nonobese diabetic (NOD) mouse immediately prior to the onset of disease (Rothe et al., *J. Clin. Invest.* 99:469, 1997). Similarly, IL-18 levels have been shown to be markedly elevated in the synovial fluid of rheumatoid arthritis patients (Kawashima et al., *Arthritis and Rheumatism* 39:598, 1996). Furthermore, it has been demonstrated that IL-18 administration increases the clinical severity of murine experimental allergic encephalomyelitis (EAE), a Th1-mediated autoimmune disease that is a model for multiple sclerosis. In addition, it has been shown that neutralizing anti-rat IL-18 antiserum prevents the development of EAE in female Lewis rats (Wildbaum et al., *J. Immunol.* 161:6368, 1998). Accordingly, IL-18 is a desirable target for the development of a novel therapeutic for autoimmunity.

Taniguchi et al., *J. Immunol. Methods* 206:107, describe seven murine and six rat anti-human IL-18 mAbs, which bind to four distinct antigenic sites. One of the murine mAbs (#125-2H), and the six rat mAbs inhibit IL-18-induced IFN-γ production by KG-1 cells, with the rat mAbs exhibiting neutralizing activities 10-fold lower than that of #125-2H. As demonstrated by Western blot analysis, three of the murine mAbs, but none of the rat mAbs, are strongly reactive with membrane-bound human IL-18. In addition, an enzyme-linked immunosorbent assay (ELISA) to detect human IL-18 is described, utilizing #125-2H and a rat mAb. The limit of detection of this ELISA is 10 pg/ml.

European patent application EP 0 712 931 discloses two mouse anti-human IL-18 mAbs, H1 (IgG1) and H2 (IgM). As demonstrated by Western blot analysis, both mAbs react with membrane-bound human IL-18, but not with membrane-bound human IL-12. HI is utilized in an immunoaffinity chromatography protocol to purify human IL-18, and in an ELISA to measure human IL-18. H2 is utilized in a radioimmunoassay to measure human IL-18.

Neutralizing IL-18 antibodies may potentially be useful in relieving autoimmune diseases and related symptoms in man. Hence there is a need in the art for a high affinity IL-18 antagonist, such as a neutralizing monoclonal antibody to human interleukin 18, which would reduce Th1 differentiation and proliferation and thus autoimmune diseases and related symptoms.

SUMMARY OF THE INVENTION

In a first aspect, the present invention provides rodent (e.g., rat and murine) neutralizing monoclonal antibodies specific for human interleukin-18 and having a binding affinity characterized by a dissociation constant equal to or less than about $3.9 \times 10^{-11}$ M as described in the detailed description. Exemplary of such monoclonal antibodies are the rat monoclonal antibody 2C10 and rat and murine monoclonal antibodies such as 14B7 and 13G9. Another aspect of the invention are hybridomas such as 19522C10 (2)F2(1)A1, 195214B7(1)H10 and 187413G9(3)F12.

In a related aspect, the present invention provides neutralizing Fab fragments or F(ab')$_2$ fragments thereof specific for human interleukin-18 produced by deleting the Fc region of the rodent neutralizing monoclonal antibodies of the present invention.

In still another related aspect, the present invention provides an altered antibody specific for human interleukin-18 which comprises complementarity determining regions (CDRs) derived from a non-human neutralizing monoclonal antibody (mAb) characterized by a dissociation constant equal to or less than about $3.9 \times 10^{-11}$ M for human interleukin-18 and nucleic acid molecules encoding the same. When the altered antibody is a humanized antibody, the sequences that encode complementarity determining regions (CDRs) from a non-human immunoglobulin are inserted into a first immunoglobulin partner in which at least one, and preferably all complementarity determining regions (CDRs) of the first immunoglobulin partner are replaced by CDRs from the non-human monoclonal antibody. Preferably, the first immunoglobulin partner is operatively linked to a second immunoglobulin partner as well, which comprises all or a part of an immunoglobulin constant chain.

In a related aspect, the present invention provides CDRs derived from non-human neutralizing monoclonal antibodies (mAbs) characterized by a dissociation constant equal to or less than about $3.9 \times 10^{-11}$ M for human interleukin-18, and nucleic acid molecules encoding such CDRs.

In still another aspect, there is provided a chimeric antibody containing human heavy and light chain constant regions and heavy and light chain variable regions derived from non-human neutralizing monoclonal antibodies characterized by a dissociation constant equal to or less than about $3.9 \times 10^{-11}$ M for human interleukin-18.

In yet another aspect, the present invention provides a pharmaceutical composition which contains one (or more) of the above described altered antibodies and a pharmaceutically acceptable carrier.

In a further aspect, the present invention provides a method for treating conditions in humans associated with excess Th1 production, for example autoimmune diseases, by administering to said human an effective amount of the pharmaceutical composition of the invention.

In yet another aspect, the present invention provides methods for, and components useful in, the recombinant production of altered antibodies (e.g., engineered antibodies, CDRs, Fab or F(ab)$_2$ fragments, or analogs thereof) which are derived from non-human neutralizing monoclonal antibodies (mAbs) characterized by a dissociation constant equal to or less than $3.9 \times 10^{-11}$ M for human IL-18. These components include isolated nucleic acid sequences encoding same, recombinant plasmids containing the nucleic acid sequences under the control of selected regulatory sequences which are capable of directing the expression thereof in host cells (preferably mammalian) transfected with the recombinant plasmids. The production method involves culturing a transfected host cell line of the present invention under conditions such that an altered antibody, preferably a humanized antibody, is expressed in said cells and isolating the expressed product therefrom.

In yet another aspect of the invention is a method to diagnose conditions associated with excess Th1 production in a human which comprises obtaining a sample of biological fluid from a patient and allowing the antibodies and altered antibodies of the instant invention to come in contact with such sample under conditions such that an IL-18/antibody (monoclonal or altered) complex is formed and detecting the presence or absence of said IL-18/antibody complex.

Other aspects and advantages of the present invention are described further in the detailed description and the preferred embodiments thereof.

BRIEF DESCRIPTION OF THE DRAWINGS

FIG. 1 [SEQ ID NOS: 1 and 2] illustrates the light chain variable region for the rat antibody 2C10. FIG. 1 includes sequence data for both strands. The boxed areas indicate the CDR's [SEQ ID NOS: 3–8]. The bolded area indicates the degenerate primer sequence.

FIG. 2. [SEQ ID NOS: 9 and 10] illustrates the heavy chain variable region or the rat antibody 2C10. FIG. 2 includes sequence data for both strands. The boxed areas indicate the CDR's [SEQ ID NOS: 11–16]. The bolded area indicates the degenerate primer sequence.

FIG. 3 [SEQ ID NOS: 17 and 18] illustrates the light chain variable region for the murine antibody 13G9. FIG. 3 includes sequence data for both strands. The boxed areas indicate the CDR's [SEQ ID NOS: 19–24]. The bolded area indicates the degenerate primer sequence.

FIG. 4 [SEQ ID NOS: 25 and 26] illustrates the heavy chain variable region for the murine antibody 13G9. FIG. 4 includes sequence data for both strands. The boxed areas indicate the CDR's [SEQ ID NOS: 27–32]. The bolded area indicates the degenerate primer sequence.

FIG. 5 [SEQ ID NOS: 33 and 34] illustrates the light chain variable region for the rat antibody 14B7. FIG. 5 includes sequence data for both strands. The boxed areas indicate the CDR's [SEQ ID NOS: 35–40]. The bolded area indicates the degenerate primer sequence.

FIG. 6 [SEQ ID NOS: 41 and 42] illustrates the heavy chain variable region for the rat antibody 14B7. FIG. 6 includes sequence data for both strands. The boxed areas indicate the CDR's [SEQ ID NOS: 43–48]. The bolded area indicates the degenerate primer sequence.

DETAILED DESCRIPTION OF THE INVENTION

The present invention provides a variety of antibodies, altered antibodies and fragments thereof, which are characterized by human IL-18 binding specificity, neutralizing activity, and high affinity for human IL-18 as exemplified in rat monoclonal antibody 2C10, murine monoclonal antibody 13G9 and rat monoclonal antibody 14B7. The antibodies of the present invention were prepared by conventional hybridoma techniques to generate novel neutralizing antibodies. These products are useful in therapeutic and pharmaceutical compositions for treating IL-18-mediated disorders, e.g. autoimmune diseases, including multiple sclerosis (MS), rheumatoid arthritis (RA), type 1, or insulin dependent, diabetes (IDDM), inflammatory bowel disease (IBD), and psoriasis (Mosmann and Sad, *Immunol. Today* 17:138, 1996). These products are also useful in the diagnosis of IL-18-mediated conditions by measurement (e.g., enzyme linked immunosorbent assay (ELISA)) of endogenous IL-18 levels in humans or IL-18 released ex vivo from activated cells.

I. Definitions.

"Altered antibody" refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, or F(ab)$_2$ and the like.

"Altered immunoglobulin coding region" refers to a nucleic acid sequence encoding altered antibody of the invention. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof.

Such CDR regions, located within the variable region of antibodies (immunoglobulins) can be determined by known methods in the art. For example Kabat et al. (*Sequences of Proteins of Immunological Interest*, 4th Ed., U.S. Department of Health and Human Services, National Institutes of Health (1987)) disclose rules for locating CDRs. In addition, computer programs are known which are useful for identifying CDR regions/structures.

"Neutralizing" refers to an antibody that inhibits IL-18 activity by preventing the binding of human IL-18 to its specific receptor or by inhibiting the signaling of IL-18 through its receptor, should binding occur. A mAb is neutralizing if it is 90% effective, preferably 95% effective and most preferably 100% effective in inhibiting IL-18 activity as measured in the IL-18 neutralization assay, see Example 1 and Table I.

The term "high affinity" refers to an antibody having a binding affinity characterized by a Kd equal to or less than $3.9 \times 10^{-11}$ M for human IL-18 as determined by optical biosensor analysis (see Example 2 and Table I).

By "binding specificity for human IL-18" is meant a higher affinity for human IL-18 than murine, or other IL-18.

"Second immunoglobulin partner" refers to another nucleotide sequence encoding a protein or peptide to which the first immunoglobulin partner is fused in frame or by means of an optional conventional linker sequence (i.e., operatively linked). Preferably it is an immunoglobulin gene. The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab)$_2$ are used with their standard meanings (see, e.g., Harlow et al., *Antibodies A LaboratorEy Manual*, Cold Spring Harbor Laboratory, (1988)).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., *Proc. Natl Acad Sci USA*, 86:10029–10032 (1989), Hodgson et al., *Bio/Technoloy*, 9:421 (1991)).

The term "donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a non-human neutralizing monoclonal antibody (i.e., rat) designated as 2C10. The antibody 2C10 is defined as a high affinity, human-IL-18 specific (i.e., does not recognize murine IL-18), neutralizing antibody of isotype IgG$_{1K}$ having the variable light chain DNA and amino acid sequences of SEQ ID NOs: 1 and 2 and respectively, the variable heavy chain DNA and amino acid sequences of SEQ ID NOs: 9 and 10 on a suitable murine IgG constant region.

The term "acceptor antibody" refers to an antibody (monoclonal, or recombinant) heterologous to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By sharing the antigen binding specificity or neutralizing ability is meant, for example, that although mAb 2C10 may be characterized by a certain level of antigen affinity, a CDR encoded by a nucleic acid sequence of 2C10 in an appropriate structural environment may have a lower, or higher affinity. It is expected that CDRs of 2C10 in such environments will nevertheless recognize the same epitope(s) as 2C10. Exemplary light chain CDRs of 2C10 include

SEQ ID NO: 3;
SEQ ID NO: 5;
SEQ ID NO: 7;

and exemplary heavy chain CDRs of 2C10 include

SEQ ID NO: 11;
SEQ ID NO: 13;
and SEQ ID NO: 15.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BlAcore [Pharnacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

II. High Affinity IL-18 Monoclonal Antibodies

For use in constructing the antibodies, altered antibodies and fragments of this invention, a non-human species (for example, bovine, ovine, monkey, chicken, rodent (e.g., murine and rat), etc.) may be employed to generate a desirable immunoglobulin upon presentment with native human IL-18 or a peptide epitope therefrom. Conventional hybridoma techniques are employed to provide a hybridoma cell line secreting a non-human mAb to IL-18. Such hybridomas are then screened for binding using IL-18 coated to 96-well plates, as described in the Examples section, or alternatively with biotinylated IL-I 8 bound to a streptavidin coated plate.

One exemplary, high affinity, neutralizing mAb of this instant invention is mAb 2C10, a rat antibody which can be used for the development of a chimeric or humanized antibody, described in more detail in examples below. The 2C10 mAb is characterized by an antigen binding specificity for human IL-18 of about $K_d$ $3.9 \times 10^{-11}$ M. This mAB is characterized by being isotype $IgG_{1,K}$.

Another desirable donor antibody is the murine mAb 13G9. This mAb is characterized by being isotype $IgG_{1K}$. The mAb has a dissociation constant for IL-18 of about $12 \times 10^9$ M.

Yet, another desirable donor antibody is the rat mAb, 14B7. This mAb is characterized by having a dissociation constant for IL-18 about $1.5 \times 10^{-10}$ M. 14B7 is also characterized by being isotype $IgG_{IK}$.

This invention is not limited to the use of the 13G9, 2C10, 14B7, or their hypervariable (i.e., CDR) sequences. Any other appropriate high affinity IL-18 antibodies characterized by a dissociation constant equal or less than about $3.9 \times 10^{-11}$ M for human IL-18 and corresponding anti-IL-18 CDRs may be substituted therefor.

Wherever in the following description the donor antibody is identified as 13G9, 2C10, 14B7, this designation is made for illustration and simplicity of description only.

III. Antibody Fragments

The present invention also includes the use of Fab fragments or $F(ab')_2$ fragments derived from mAbs directed against human IL-18. These fragments are useful as agents protective in vivo against IL-18 and Th 1-mediated conditions or in vitro as part of an IL-18 diagnostic. A Fab fragment contains the entire light chain and amino terminal portion of the heavy chain; and an $F(ab')_2$ fragment is the fragment formed by two Fab fragments bound by disulfide bonds. MAbs 13G9, 2C10, 14B7, and other similar high affinity, IL-18 binding antibodies, provide sources of Fab fragments and $F(ab')_2$ fragments which can be obtained by conventional means, e.g., cleavage of the mAb with the appropriate proteolytic enzymes, papain and/or pepsin, or by recombinant methods. These Fab and $F(ab')_2$ fragments are useful themselves as therapeutic, prophylactic or diagnostic agents, and as donors of sequences including the variable regions and CDR sequences useful in the formation of recombinant or humanized antibodies as described herein.

The Fab and $F(ab')_2$ fragments can be constructed via a combinatorial phage library (see, e.g., Winter et al., *Ann. Rev. Immunol.*, 12:433–455 (1994)) or via immunoglobulin chain shuffling (see, e.g., Marks et al., *Bio/TechnologW*, 10:779–783 (1992), which are both hereby incorporated by reference in their entirety) wherein the Fd or $V_H$ immunoglobulin from a selected antibody (e.g., 13G9) is allowed to associate with a repertoire of light chain immunoglobulins, $V_L$ (or $V_K$), to form novel Fabs. Conversely, the light chain immunoglobulin from a selected antibody may be allowed to associate with a repertoire of heavy chain immunoglobulins, $V_H$ (or Fd), to form novel Fabs.

IV. Anti-IL-18 Amino Acid and Nucleotide Sequences of Interest

The mAb 2C10 or other antibodies described above may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

As one example, the present invention provides variable light chain and variable heavy chain sequences from the IL-18 mAb 2C10 and sequences derived therefrom.

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression.

Taking into account the degeneracy of the genetic code, various coding sequences may be constructed which encode the variable heavy and light chain amino acid sequences, and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies, or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions [see, T. Maniatis et al, *Molecular Cloning (A Laboratory Manual*), Cold Spring Harbor Laboratory (1982), pages 387 to 389] to the DNA sequences. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C. Preferably, these hybridizing DNA sequences are at least about 18 nucleotides in length, i.e., about the size of a CDR.

V. Altered Immunoglobulin Molecules And Altered Antibodies

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an IL-18 antibody, preferably a high affinity antibody such as provided by the present invention, inserted into a first immunoglobulin partner (a human framework or human immunoglobulin variable region).

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of IL-18 may be designed to elicit enhanced binding with the same antibody.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified to enhance expression.

An exemplary altered antibody contains a variable heavy and/or light chain peptide or protein sequence having the antigen specificity of mAb 2C10, e.g., the $V_H$ and $V_L$ chains. Still another desirable altered antibody of this invention is characterized by the amino acid sequence containing at least one, and preferably all of the CDRs of the variable region of the heavy and/or light chains of the rat antibody molecule 2C10 with the remaining sequences being derived from a human source, or a functional fragment or analog thereof.

In still a further embodiment, the engineered antibody of the invention may have attached to it an additional agent. For example, the procedure of recombinant DNA technology may be used to produce an engineered antibody of the invention in which the Fc fragment or CH2 CH3 domain of a complete antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence, for example, having the antigen specificity of rat 2C10. The resulting protein may exhibit both anti-IL-18 antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an $F_v$ or a single-chain antibody (SCA) or any other molecule with the same specificity as the selected donor mAb, e.g., mAb 2C10. Such protein may be used in the form of an altered antibody, or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody, e.g., the anti-IL-18 antibody described herein. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the IL-18 mAb (optionally modified as described) or one or more of the below-identified heavy or light chain CDRs. The engineered antibodies would be expected to be are neutralizing, i.e., they desirably block binding to the receptor of the IL-18 protein and they also block or prevent proliferation of IL-18 dependent cells.

Such engineered antibodies may include a humanized antibody containing the framework regions of a selected human immunoglobulin or subtype, or a chimeric antibody containing the human heavy and light chain constant regions fused to the IL-18 antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

One example of a particularly desirable humanized antibody would contain CDRs of 2C10 inserted onto the framework regions of a selected human antibody sequence. For neutralizing humanized antibodies, one, two or preferably three CDRs from the IL-18 antibody heavy chain and/or light chain variable regions are inserted into the framework regions of the selected human antibody sequence, replacing the native CDRs of the latter antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of IL-18 mediated inflammatory diseases in man, or for diagnostic uses.

As another example, an engineered antibody may contain CDRs of the variable light chain region of 2C10 and CDRs of the variable heavy chain region of 13G9. The resulting humanized antibody should be characterized by the same antigen binding specificity and high affinity of mAb 2C10.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., *Mol. Immunol*, 30:105–108 (1993), Xu et al., *J. Biol. Chem*, 269:3469–3474 (1994), Winter et al., EP 307,434-B).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant immune response in humans.

Such antibodies could be useful in the prevention and treatment of IL-18 mediated disorders, as discussed below.

VI. Production Of Altered Antibodies And Engineered Antibodies

Preferably, the variable light and/or heavy chain sequences and the CDRs of mAb 2C10 or other suitable donor mAbs, and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the rat antibody 2C10, is conventionally cloned, and the DNA of its heavy and light chain variable regions obtained by techniques known to one of skill in the art, e.g., the techniques described in Sambrook et al., (*Molecular Cloning (A Laboratory Manual)*, 2nd edition, Cold Spring Harbor Laboratory (1989)). The variable heavy and light regions of 2C10 containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin can be obtained using polynucleotide primers and reverse transcriptase. The CDR-encoding regions are identified using a known database and by comparison to other antibodies.

A rat/human chimeric antibody may then be prepared and assayed for binding ability. Such a chimeric antibody contains the entire non-human donor antibody $V_H$ and $V_L$ regions, in association with human Ig constant regions for both chains.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention may be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells. Other humanized antibodies may be prepared using this technique on other suitable IL-18-specific, neutralizing, high affinity, non-human antibodies.

A conventional expression vector or recombinant plasmid can be produced by placing these coding sequences for the altered antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by appropriate assay, such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the conventional pUC series of cloning vectors, may be used. One vector used is pUC19, which is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV promoters) which direct the replication and expression of heterologous DNA sequences in selected host cells. These vectors contain the above described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3), and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Pluckthun, A., *Immunol. Rev.*, 130:151–188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis*, Streptomyces, other bacilli and the like may also be employed in this method.

Where desired, strains of yeast cells known to those skilled in the art are also available as host cells, as well as insect cells, e.g. Drosophila and Lepidoptera and viral expression systems. See, e.g. Miller et al., *Genetic Engineering*, 8:277–298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently conventional ELISA assay formats are employed to assess qualitative and quantitative binding of the engineered antibody to IL-18. Additionally, other in vitro assays may also be used to verify neutralizing efficacy prior to subsequent human clinical studies performed to evaluate the persistence of the engineered antibody in the body despite the usual clearance mechanisms.

Following the general procedures described for preparing humanized antibodies, one of skill in the art may also construct humanized antibodies from other donor IL-18 antibodies, variable region sequences and CDR peptides described herein. Engineered antibodies can be produced with variable region frameworks potentially recognized as "self" by recipients of the engineered antibody. Minor modifications to the variable region frameworks can be implemented to effect large increases in antigen binding without appreciable increased immunogenicity for the recipient. Such engineered antibodies may effectively treat a human for IL-18 mediated conditions. Such antibodies may also be useful in the diagnosis of such conditions.

VII. Therapeutic/Prophylactic Uses

This invention also relates to a method of treating humans experiencing autoimmune related symptoms, such as MS, which comprises administering an effective dose of antibodies including one or more of the engineered antibodies or altered antibodies described herein, or fragments thereof.

The therapeutic response induced by the use of the molecules of this invention is produced by the binding to human IL-18 and thus subsequently blocking Th1 stimulation. Thus, the molecules of the present invention, when in preparations and formulations appropriate for therapeutic use, are highly desirable for those persons experiencing autoimmune disease, such as but not limited to MS, RA, IDDM, IBD and psoriasis.

The altered antibodies, antibodies and fragments thereof of this invention may also be used in conjunction with other antibodies, particularly human mabs reactive with other markers (epitopes) responsible for the condition against which the engineered antibody of the invention is directed.

The therapeutic agents of this invention are believed to be desirable for treatment of autoimmune conditions from about 2 days to 6 months or as needed. For example, longer treatments may be desirable when treating MS or the like. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously, or intranasaly.

Therapeutic agents of the invention may be prepared as pharmaceutical compositions containing an effective amount of the engineered (e.g., humanized) antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat an inflammatory disorder in a human or other animal, one dose of approximately 0.1 mg to approximately 20 mg per 70 kg body weight of a protein or an antibody of this invention should be administered parenterally, preferably i.v. or i.m. (intramuscularly). Such dose may, if necessary, be repeated at appropriate time intervals selected as appropriate by a physician during the disease.

The altered antibodies and engineered antibodies of this invention may also be used in diagnostic regimens, such as for the determination of IL-18 mediated disorders or tracking progress of treatment of such disorders. As diagnostic reagents, these altered antibodies may be conventionally labeled for use in ELISA's and other conventional assay formats for the measurement of IL-18 levels in serum, plasma or other appropriate tissue, or the release by human cells in culture. The nature of the assay in which the altered antibodies are used are conventional and do not limit this disclosure.

Thus, one embodiment of the present invention relates to a method for aiding the diagnosis of autoimmune disease and other conditions associated with excess Th1 T cell production in a patient which comprises the steps of determining the amount of human IL-18 in sample (plasma or tissue) obtained from said patient and comparing said determined amount to the mean amount of human IL-18 in the normal population, whereby the presence of a significantly elevated amount of IL-18 in the patient's sample is an indication autoimmune disease and other conditions associated with excess Th1 T cell production.

The antibodies, altered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

The following examples illustrate various aspects of this invention including the construction of exemplary engineered antibodies and expression thereof in suitable vectors and host cells, and are not to be construed as limiting the scope of this invention. All amino acids are identified by conventional three letter or single letter codes. All necessary restriction enzymes, plasmids, and other reagents and materials were obtained from commercial sources unless otherwise indicated. All general cloning legation and other recombinant DNA methodology were as performed in T. Maniatis et al., cited above, or the second edition thereof (1989), eds. Sambrook et al., by the same publisher ("Sambrook et al.").

EXAMPLE 1

Production of MAbs to IL-18

A. Monoclonal Antibody Generation

Mice (F1 hybrids of Balb/c and C57B1U6) or rats (Sprague Dawley) were immunised with 30 μg recombinant IL-18 in adjuvant and 4 weeks later with 30 μg IL-18 in adjuvant. On the basis of a good serum antibody titre to IL-18 animals received a further immunization of 10–30 μg IL-18 (i.p. in saline). Three days following the final immunization a splenectomy was performed. Mouse or rat spleen cells were used to prepare hybridomas by standard procedures, (Zola, H.Ed., Monoclonal Antibodies, CRC Press Inc. 1987). Positive hybridomas were cloned by the limiting dilution method.

B. Purification of Mabs

Mabs were purified by ProsepA (Bio Processing, Consett, UK) chromatography respectively using the manufacturer's instructions. Mabs were >95% pure by SDS-PAGE.

C. Isotyping of Mabs

All rat and mouse Mabs were isotyped by commercially available kits (Zymed, Amersham) and found to be IgG1 kappa.

EXAMPLE 2

Assays

A. Biotinylation Of Il-18

IL-18 was biotinylated using a kit purchased from Molecular Probes Inc. using a 10:1 ratio of biotinylation reagent. Biotinylation had no effect on the biological activity of IL-18

B. Hybridoma Screening Assay 96-well plates were coated with streptavidin (2 ug/ml, 100 ul/well in PBS) by incubation overnight at 4° C. The solution was then aspirated and non-specific binding sites were blocked with 250 ul/well of 1% bovine serum albumin (BSA) in TBS buffer (SOmM Tris, 150 mM NaCl, 0.02% Kathon, pH 7.4) for 5–60 minutes at RT. Following this and each of the following steps, the plate was washed 4 times in wash buffer (10 mM Tris, 150 mM NaCl, 0.05% Tween 20, 0.02% Kathon, pH 7.4). To each well, 100 $\mu$L biotin IL-18 (100 ng/ml) in assay buffer (0.5% BSA, 0.05% bovine gamma globulin, 0.01% Tween 40, 20CM diethylenetriaminepentaacetic in TBS buffer) was added and the plates were incubated for 30 min at RT in a shaker-incubator. To each well 50$\mu$l hybridoma medium and 50 $\mu$l assay buffer was then added and incubated for 60 min at RT in a shaker-incubator. To each well was then added 100 ul 0.5 $\mu$g/ml $Eu^{3+}$ labelled anti-mouse or anti-rat antibody in assay buffer. Finally 200 $\mu$l /well of enhancer (Wallac) was added and incubated for 5 min at RT and the time-resolved fluorescence measured. Hybridomas having counts >100K were expanded into 24-well plates.

C. Immunoassay

To determine the specificity of the anti-IL-18 Mabs) generated 96-well plates were coated, blocked and incubated with biotin IL-18 as above. All the following incubations were performed in a shaker-incubator at RT. After washing the wells 50 $\mu$l IL-18 (3 $\mu$g/ml) or assay buffer and 50 $\mu$l Mab were added and incubated for 60 min. After washing the wells 100 ul 0.5 $\mu$g/ml $Eu^{3+}$ labelled anti-mouse or anti-rat antibody in assay buffer was added for 60 min, the wells washed and then 100 $\mu$l/well of enhancer (Wallac) was added and incubated for 5 min at RT and the time-resolved fluorescence measured. All positive hybridomas showed displacement of binding with EL-18.

D. Neutralization Assay

PBMC from healthy donors were isolated by Ficol-Paque (Pharmacia) gradient and cultured in 96 well plates in 10% FBS DMEM/F12 media with 1 $\mu$g/ml ConA (Sigma) in the presence of IL-18 (5ng/ml) and/or Mabs. After 18 h culture at 37° C., 5% $CO_2$ in air, 90% humidity 25 $\mu$l media was removed and interferon gamma (IFNg) concentration measured by immunoassay. The results, obtained from an average of three experiments, are summarized in Table I.

E. Affinity Measurements of Monoclonal Antibody

The affinity of the purified mabs was measured in the BIAcore optical biosensor (Pharmacia Biosensor, Uppsala, Sweden) using a flow rate of 30 ul/min. Kinetic data was evaluated using relationships described previously (Karlsson et al, *J. Immunol. Meth.*, 145:229–240 (1991) and which is incorporated by reference in its entirely. The mAb (diluted in HBS buffer, 10 mM HEPES, 150 rnM NaCl, 0.01% Tween-20, pH 7.4) was injected over a rabbit anti-mouse IgG Fc or goat anti-rat IgG Fc surface, followed by buffer flow and the RU was recorded. IL-18 (diluted in HBS buffer) was then injected for 180 seconds followed by a buffer flow for 500 seconds and the RU was recorded. The sensor chip surface was regenerated by an injection of 0.1 M phosphoric acid. The on-rates (Kass) and off-rates (Kdiss) of binding were calculated using BIAcore software and together these yield a calculated equilibrium constant ($K_D$) of $12 \times 10^{-9}$ M for mAb 13G9, $3.9 \times 10^{-11}$ M for mAb 2C10 and $1.5 \times 10^{-10}$ M for mAb 14B7. See Table I.

F. Epitope Analysis of Monoclonal Antibody

The epitope analysis of the purified Mabs was measured in the BIAcore. Using a flow rate of 10 $\mu$l/min, the first Mab (diluted in HBS buffer) was injected over a rabbit anti-mouse IgG Fc or goat anti-rat IgG Fc surface, followed by an injection of IL-18 for 240s, an injection of blocking Mabs for 48s and an injection of the second Mab for 240s. The surface was regenerated by an injection of 0.1 M phosphoric acid and the RU was recorded after each injection. It was found that Mabs 13G9, 2C10 and 14B7 have similar or overlapping epitopes.

TABLE I

Affinity and neutralizing activity of mAbs reactive with human IL-18

| mAb | Kd (pM)[a] | Neutralisation IC50 (nM)[b] |
|---|---|---|
| 2C10 (rat) | 39 | 0.1 |
| 14B7 (rat) | 150 | 0.2 |
| 13G9 (mouse) | 12000 | 3.0 |

[a]Determined by optical biosensor (BIAcore) analysis (25° C.)
[b]Inhibition of IFN gamma production (in nM) of PBMC in response to 5 ng/ml human IL-18

EXAMPLE 3

CDR Sequences

Gene Cloning and Sequence Analysis:

The variable heavy and light genes were cloned from hybridoma cells using standard molecular biological methods described briefly as follows. Total RNA was isolated from the hybridoma cells using TRIzol Reagent (Life Technologies Cat. #15596–026) according to manufacturer's protocol. The RNA was reverse transcribed with a RT-PCR kit per the manufacturer's instructions (Boehringer Mannheim Cat. No. 1483-188) using a poly-dT oligonucleotide for priming. Following first strand cDNA synthesis, the heavy and light V regions were PCR amplified using 3' constant region specific primers and degenerate 5' primers. The degenerate 5' primer sequences were designed to encode the previously determined N terminal amino acid sequences of the variable heavy or light chain regions. Full length sequences from multiple clones were obtained from each PCR amplification and aligned to provide consensus. Accordingly, the first 17 bases of DNA sequence for both the heavy and light chains are PCR primer generated, however the translated protein sequence is native.

The nucleotide and deduced amino acid sequences for hybridoma antibodies 2C10, 13G9, and 14B7 are shown FIGS. 1–6. In each case the CDR s and the nucleotide sequences encoding them are boxed. The degenerate primer sequences are bolded.

What is claimed is:

1. A monoclonal antibody specific for human IL-18, wherein said monoclonal antibody comprises the light chain amino acid sequence of SEQ ID NO: 2 and the heavy chain amino acid sequence of SEQ ID NO: 10.

2. A hybridoma which produces the monoclonal antibody of claim 1.

3. A neutralizing Fab fragment or F(ab')$_2$ fragment thereof, produced by deleting the Fc region of the monoclonal antibody of claim 1.

4. A method to assess the presence or absence of human IL-18 in a human, said method comprising the steps of: (a) obtaining a sample of biological fluid from a human and allowing the monoclonal antibody of claim 4 to come in contact with such sample under conditions, such that an IL-I 8/monoclonal antibody complex can form; and (2) detecting the presence or absence of said IL-18/monoclonal antibody complex.

5. An immunoglobulin light chain complementarity determining region (CDR), the amino acid sequence of which is isolated and is chosen from the group of:

(a) SEQ ID NO: 4;

(b) SEQ ID NO: 6; and (c) SEQ ID NO: 8.

6. An isolated nucleic acid molecule encoding the immunoglobulin complementarity determining region (CDR) of claim 5.

7. An immunoglobulin heavy chain complementarity determining region (CDR), the amino acid sequence of which is isolated and is chosen from the group of:

(a) SEQ ID NO: 12;

(b) SEQ ID NO: 14; and (c) SEQ ID NO: 16.

8. An isolated nucleic acid molecule encoding the immunoglobulin complementarity determining region (CDR) of claim 7.

* * * * *

UNITED STATES PATENT AND TRADEMARK OFFICE
CERTIFICATE OF CORRECTION

PATENT NO. : 6,706,487 B1
DATED : March 16, 2004
INVENTOR(S) : Sherin S. Abdel-Meguid et al.

It is certified that error appears in the above-identified patent and that said Letters Patent is hereby corrected as shown below:

<u>Title page,</u>
Item [73], Assignees, should be: -- SmithKline Beecham Corporation, Philadelphia, PA (US) and SmithKline Beecham p.l.c., Brentford, Middlesex, United Kingdom (UK) --

Signed and Sealed this

Thirteenth Day of July, 2004

JON W. DUDAS
*Acting Director of the United States Patent and Trademark Office*

SEQUENCE LISTING

<160> NUMBER OF SEQ ID NOS: 48

<210> SEQ ID NO 1
<211> LENGTH: 324
<212> TYPE: DNA
<213> ORGANISM: Rattus norvegicus
<220> FEATURE:
<221> NAME/KEY: CDS
<222> LOCATION: (1)...(324)
<223> OTHER INFORMATION: Light Chain V Region

<400> SEQUENCE: 1

```
gac att caa atg acc cag tct cca gct tcc ctg tct gca tct ctg gga      48
Asp Ile Gln Met Thr Gln Ser Pro Ala Ser Leu Ser Ala Ser Leu Gly
 1               5                  10                  15 gaa act gtc tcc atc gaa tgt ctg gca agt gag gac ata tac act tat      96
Glu Thr Val Ser Ile Glu Cys Leu Ala Ser Glu Asp Ile Tyr Thr Tyr
                20                  25                  30 tta aca tgg tat cag cag aaa cca ggg aaa tct cct caa ctc ctg atc     144
Leu Thr Trp Tyr Gln Gln Lys Pro Gly Lys Ser Pro Gln Leu Leu Ile
             35                  40                  45 tat ggt gca aat aag ttg caa gat ggg gtc cca tca cgg ttc agt ggc     192
Tyr Gly Ala Asn Lys Leu Gln Asp Gly Val Pro Ser Arg Phe Ser Gly
         50                  55                  60 agt gga tct ggc aca cag tat tct ctc aag atc agc ggc ata caa cct     240
Ser Gly Ser Gly Thr Gln Tyr Ser Leu Lys Ile Ser Gly Ile Gln Pro
 65                  70                  75                  80 gaa gat gaa ggg gat tat ttc tgt cta cag ggt tcc aag ttt ccg ctc     288
Glu Asp Glu Gly Asp Tyr Phe Cys Leu Gln Gly Ser Lys Phe Pro Leu
                 85                  90                  95 acg ttc ggt tct ggg acc aag ctg gag atc aaa cgg                     324
Thr Phe Gly Ser Gly Thr Lys Leu Glu Ile Lys Arg
                100                 105
```

<210> SEQ ID NO 2
<211> LENGTH: 108
<212> TYPE: PRT
<213> ORGANISM: Rattus norvegicus

<400> SEQUENCE: 2

```
Asp Ile Gln Met Thr Gln Ser Pro Ala Ser Leu Ser Ala Ser Leu Gly
 1               5                  10                  15

Glu Thr Val Ser Ile Glu Cys Leu Ala Ser Glu Asp Ile Tyr Thr Tyr
                20                  25                  30

Leu Thr Trp Tyr Gln Gln Lys Pro Gly Lys Ser Pro Gln Leu Leu Ile
             35                  40                  45

Tyr Gly Ala Asn Lys Leu Gln Asp Gly Val Pro Ser Arg Phe Ser Gly
         50                  55                  60

Ser Gly Ser Gly Thr Gln Tyr Ser Leu Lys Ile Ser Gly Ile Gln Pro
 65                  70                  75                  80

Glu Asp Glu Gly Asp Tyr Phe Cys Leu Gln Gly Ser Lys Phe Pro Leu
                 85                  90                  95

Thr Phe Gly Ser Gly Thr Lys Leu Glu Ile Lys Arg
                100                 105
```

<210> SEQ ID NO 3
<211> LENGTH: 33
<212> TYPE: DNA
<213> ORGANISM: Rattus norvegicus
<220> FEATURE:

```
<221> NAME/KEY: CDS
<222> LOCATION: (1)...(33)
<223> OTHER INFORMATION: VK2C10 Light Chain CDR I

<400> SEQUENCE: 3 ctg gca agt gag gac ata tac act tat tta aca                33
Leu Ala Ser Glu Asp Ile Tyr Thr Tyr Leu Thr
1               5                   10

<210> SEQ ID NO 4
<211> LENGTH: 11
<212> TYPE: PRT
<213> ORGANISM: Rattus norvegicus

<400> SEQUENCE: 4

Leu Ala Ser Glu Asp Ile Tyr Thr Tyr Leu Thr
1               5                   10

<210> SEQ ID NO 5
<211> LENGTH: 21
<212> TYPE: DNA
<213> ORGANISM: Rattus norvegicus
<220> FEATURE:
<221> NAME/KEY: CDS
<222> LOCATION: (1)...(21)
<223> OTHER INFORMATION: VK2C10 Light Chain CDR II

<400> SEQUENCE: 5 ggt gca aat aag ttg caa gat                                21
Gly Ala Asn Lys Leu Gln Asp
1               5

<210> SEQ ID NO 6
<211> LENGTH: 7
<212> TYPE: PRT
<213> ORGANISM: Rattus norvegicus

<400> SEQUENCE: 6

Gly Ala Asn Lys Leu Gln Asp
1               5

<210> SEQ ID NO 7
<211> LENGTH: 27
<212> TYPE: DNA
<213> ORGANISM: Rattus norvegicus
<220> FEATURE:
<221> NAME/KEY: CDS
<222> LOCATION: (1)...(27)
<223> OTHER INFORMATION: VK2C10 Light Chain CDR III

<400> SEQUENCE: 7 cta cag ggt tcc aag ttt ccg ctc acg                        27
Leu Gln Gly Ser Lys Phe Pro Leu Thr
1               5

<210> SEQ ID NO 8
<211> LENGTH: 9
<212> TYPE: PRT
<213> ORGANISM: Rattus norvegicus

<400> SEQUENCE: 8

Leu Gln Gly Ser Lys Phe Pro Leu Thr
1               5

<210> SEQ ID NO 9
<211> LENGTH: 378
<212> TYPE: DNA
```

<213> ORGANISM: Rattus norvegicus
<220> FEATURE:
<221> NAME/KEY: CDS
<222> LOCATION: (1)...(378)
<223> OTHER INFORMATION: Heavy Chain V Region

<400> SEQUENCE: 9

| gag | gtc | cag | cta | cag | cag | tct | ggg | gct | gag | ctt | gtg | aga | cct | ggg | acc | 48 |
|---|---|---|---|---|---|---|---|---|---|---|---|---|---|---|---|---|
| Glu | Val | Gln | Leu | Gln | Gln | Ser | Gly | Ala | Glu | Leu | Val | Arg | Pro | Gly | Thr | |
| 1 | | | | 5 | | | | | 10 | | | | | 15 | | |

| tct | gtg | aag | tta | tct | tgc | aaa | gtt | tct | ggc | gaa | ata | agt | aca | gga | tac | 96 |
|---|---|---|---|---|---|---|---|---|---|---|---|---|---|---|---|---|
| Ser | Val | Lys | Leu | Ser | Cys | Lys | Val | Ser | Gly | Glu | Ile | Ser | Thr | Gly | Tyr | |
| | | 20 | | | | | 25 | | | | | 30 | | | | |

| tat | ttc | cac | ttt | gtg | agg | cga | agg | cct | gga | cag | ggt | ctg | gaa | tgg | ata | 144 |
|---|---|---|---|---|---|---|---|---|---|---|---|---|---|---|---|---|
| Tyr | Phe | His | Phe | Val | Arg | Arg | Arg | Pro | Gly | Gln | Gly | Leu | Glu | Trp | Ile | |
| | | 35 | | | | | 40 | | | | | 45 | | | | |

| gga | agg | att | gat | cct | gag | gat | gat | agt | act | aaa | tat | gct | gag | agg | ttc | 192 |
|---|---|---|---|---|---|---|---|---|---|---|---|---|---|---|---|---|
| Gly | Arg | Ile | Asp | Pro | Glu | Asp | Asp | Ser | Thr | Lys | Tyr | Ala | Glu | Arg | Phe | |
| 50 | | | | | 55 | | | | | 60 | | | | | | |

| aaa | gac | agg | gcg | acg | ctc | act | gca | caa | aca | tcc | tcc | aac | aca | gcc | tac | 240 |
|---|---|---|---|---|---|---|---|---|---|---|---|---|---|---|---|---|
| Lys | Asp | Arg | Ala | Thr | Leu | Thr | Ala | Gln | Thr | Ser | Ser | Asn | Thr | Ala | Tyr | |
| 65 | | | | 70 | | | | | 75 | | | | | 80 | | |

| ctg | aac | ctc | agc | agc | ctg | acc | tct | gag | gac | act | gca | act | tat | ttt | tgt | 288 |
|---|---|---|---|---|---|---|---|---|---|---|---|---|---|---|---|---|
| Leu | Asn | Leu | Ser | Ser | Leu | Thr | Ser | Glu | Asp | Thr | Ala | Thr | Tyr | Phe | Cys | |
| | | | | 85 | | | | | 90 | | | | | 95 | | |

| acc | aca | tgg | cgg | ata | tac | cga | gat | agt | tct | ggc | cgc | ccc | ttc | tat | gtt | 336 |
|---|---|---|---|---|---|---|---|---|---|---|---|---|---|---|---|---|
| Thr | Thr | Trp | Arg | Ile | Tyr | Arg | Asp | Ser | Ser | Gly | Arg | Pro | Phe | Tyr | Val | |
| | | | | 100 | | | | | 105 | | | | | 110 | | |

| atg | gat | gcc | tgg | ggt | caa | gga | gct | tca | gtc | act | gtc | tcc | tca | | | 378 |
|---|---|---|---|---|---|---|---|---|---|---|---|---|---|---|---|---|
| Met | Asp | Ala | Trp | Gly | Gln | Gly | Ala | Ser | Val | Thr | Val | Ser | Ser | | | |
| | | 115 | | | | | 120 | | | | | 125 | | | | |

<210> SEQ ID NO 10
<211> LENGTH: 126
<212> TYPE: PRT
<213> ORGANISM: Rattus norvegicus

<400> SEQUENCE: 10

Glu Val Gln Leu Gln Gln Ser Gly Ala Glu Leu Val Arg Pro Gly Thr
1               5                   10                  15

Ser Val Lys Leu Ser Cys Lys Val Ser Gly Glu Ile Ser Thr Gly Tyr
            20                  25                  30

Tyr Phe His Phe Val Arg Arg Arg Pro Gly Gln Gly Leu Glu Trp Ile
        35                  40                  45

Gly Arg Ile Asp Pro Glu Asp Asp Ser Thr Lys Tyr Ala Glu Arg Phe
    50                  55                  60

Lys Asp Arg Ala Thr Leu Thr Ala Gln Thr Ser Ser Asn Thr Ala Tyr
65                  70                  75                  80

Leu Asn Leu Ser Ser Leu Thr Ser Glu Asp Thr Ala Thr Tyr Phe Cys
                85                  90                  95

Thr Thr Trp Arg Ile Tyr Arg Asp Ser Ser Gly Arg Pro Phe Tyr Val
                100                 105                 110

Met Asp Ala Trp Gly Gln Gly Ala Ser Val Thr Val Ser Ser
        115                 120                 125

<210> SEQ ID NO 11
<211> LENGTH: 15
<212> TYPE: DNA
<213> ORGANISM: Rattus norvegicus
<220> FEATURE:
<221> NAME/KEY: CDS

```
<222> LOCATION: (1)...(15)
<223> OTHER INFORMATION: VH2C10 Heavy Chain CDR I

<400> SEQUENCE: 11 gga tac tat ttc cac                                              15
Gly Tyr Tyr Phe His
 1               5

<210> SEQ ID NO 12
<211> LENGTH: 5
<212> TYPE: PRT
<213> ORGANISM: Rattus norvegicus

<400> SEQUENCE: 12

Gly Tyr Tyr Phe His
 1               5

<210> SEQ ID NO 13
<211> LENGTH: 51
<212> TYPE: DNA
<213> ORGANISM: Rattus norvegicus
<220> FEATURE:
<221> NAME/KEY: CDS
<222> LOCATION: (1)...(51)
<223> OTHER INFORMATION: VH2C10 Heavy Chain CDR II

<400> SEQUENCE: 13 agg att gat cct gag gat gat agt act aaa tat gct gag agg ttc aaa   48
Arg Ile Asp Pro Glu Asp Asp Ser Thr Lys Tyr Ala Glu Arg Phe Lys
 1               5                  10                  15 gac                                                              51
Asp

<210> SEQ ID NO 14
<211> LENGTH: 17
<212> TYPE: PRT
<213> ORGANISM: Rattus norvegicus

<400> SEQUENCE: 14

Arg Ile Asp Pro Glu Asp Asp Ser Thr Lys Tyr Ala Glu Arg Phe Lys
 1               5                  10                  15

Asp

<210> SEQ ID NO 15
<211> LENGTH: 51
<212> TYPE: DNA
<213> ORGANISM: Rattus norvegicus
<220> FEATURE:
<221> NAME/KEY: CDS
<222> LOCATION: (1)...(51)
<223> OTHER INFORMATION: VH2C10 Heavy Chain CDR III

<400> SEQUENCE: 15 tgg cgg ata tac cga gat agt tct ggc cgc ccc ttc tat gtt atg gat   48
Trp Arg Ile Tyr Arg Asp Ser Ser Gly Arg Pro Phe Tyr Val Met Asp
 1               5                  10                  15 gcc                                                              51
Ala

<210> SEQ ID NO 16
<211> LENGTH: 17
<212> TYPE: PRT
<213> ORGANISM: Rattus norvegicus

<400> SEQUENCE: 16
```

```
Trp Arg Ile Tyr Arg Asp Ser Ser Gly Arg Pro Phe Tyr Val Met Asp
 1               5                  10                 15
Ala
```

<210> SEQ ID NO 17
<211> LENGTH: 342
<212> TYPE: DNA
<213> ORGANISM: Mus musculus
<220> FEATURE:
<221> NAME/KEY: CDS
<222> LOCATION: (1)...(342)
<223> OTHER INFORMATION: Light Chain V region

<400> SEQUENCE: 17

```
gac gtt gtt atg act caa act cct ctc tcc ctg cct gtc agt ctt gga      48
Asp Val Val Met Thr Gln Thr Pro Leu Ser Leu Pro Val Ser Leu Gly
 1               5                  10                 15 gat caa gcc tcc atc tct tgc aga tct agt cag agc ctt gta cac agt      96
Asp Gln Ala Ser Ile Ser Cys Arg Ser Ser Gln Ser Leu Val His Ser
                20                  25                  30 aat gga aac acc tat tta cat tgg tac ctg cag aag cca ggc cag tct     144
Asn Gly Asn Thr Tyr Leu His Trp Tyr Leu Gln Lys Pro Gly Gln Ser
         35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
 50                  55                  60 gac agg ttc agt ggc agt gga tca ggt aca gat ttc aca ctc aag atc     240
Asp Arg Phe Ser Gly Ser Gly Ser Gly Thr Asp Phe Thr Leu Lys Ile
 65                  70                  75                  80 agc aga gtg gag gct gag gat ctg gga gtt tat ttc tgc tct caa agt     288
Ser Arg Val Glu Ala Glu Asp Leu Gly Val Tyr Phe Cys Ser Gln Ser
                 85                  90                  95 aca cat gtt cct ccg tac acg ttc gga ggg ggg acc aag ctg gaa ata     336
Thr His Val Pro Pro Tyr Thr Phe Gly Gly Gly Thr Lys Leu Glu Ile
                100                 105                 110 aaa cgg                                                             342
Lys Arg
```

<210> SEQ ID NO 18
<211> LENGTH: 114
<212> TYPE: PRT
<213> ORGANISM: Mus musculus

<400> SEQUENCE: 18

```
Asp Val Val Met Thr Gln Thr Pro Leu Ser Leu Pro Val Ser Leu Gly
 1               5                  10                 15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Tyr Thr Phe Gly Gly Gly Thr Lys Leu Glu Ile
                100                 105                 110

Lys Arg
```

```
<210> SEQ ID NO 19
<211> LENGTH: 48
<212> TYPE: DNA
<213> ORGANISM: Mus musculus
<220> FEATURE:
<221> NAME/KEY: CDS
<222> LOCATION: (1)...(48)
<223> OTHER INFORMATION: VK13G9 Light Chain CDR I

<400> SEQUENCE: 19 aga tct agt cag agc ctt gta cac agt aat gga aac acc tat tta cat    48
Arg Ser Ser Gln Ser Leu Val His Ser Asn Gly Asn Thr Tyr Leu His
 1               5                  10                  15

<210> SEQ ID NO 20
<211> LENGTH: 16
<212> TYPE: PRT
<213> ORGANISM: Mus musculus

<400> SEQUENCE: 20

Arg Ser Ser Gln Ser Leu Val His Ser Asn Gly Asn Thr Tyr Leu His
 1               5                  10                  15

<210> SEQ ID NO 21
<211> LENGTH: 21
<212> TYPE: DNA
<213> ORGANISM: Mus musculus
<220> FEATURE:
<221> NAME/KEY: CDS
<222> LOCATION: (1)...(21)
<223> OTHER INFORMATION: VK13G9 Light Chain CDR II

<400> SEQUENCE: 21 aaa gtt tcc aac cga ttt tct                                        21
Lys Val Ser Asn Arg Phe Ser
 1               5

<210> SEQ ID NO 22
<211> LENGTH: 7
<212> TYPE: PRT
<213> ORGANISM: Mus musculus

<400> SEQUENCE: 22

Lys Val Ser Asn Arg Phe Ser
 1               5

<210> SEQ ID NO 23
<211> LENGTH: 30
<212> TYPE: DNA
<213> ORGANISM: Mus musculus
<220> FEATURE:
<221> NAME/KEY: CDS
<222> LOCATION: (1)...(30)
<223> OTHER INFORMATION: VK13G9 Light Chain CDR III

<400> SEQUENCE: 23 tct caa agt aca cat gtt cct ccg tac acg                            30
Ser Gln Ser Thr His Val Pro Pro Tyr Thr
 1               5                  10

<210> SEQ ID NO 24
<211> LENGTH: 10
<212> TYPE: PRT
<213> ORGANISM: Mus musculus

<400> SEQUENCE: 24

Ser Gln Ser Thr His Val Pro Pro Tyr Thr
```

<210> SEQ ID NO 25
<211> LENGTH: 369
<212> TYPE: DNA
<213> ORGANISM: Mus musculus
<220> FEATURE:
<221> NAME/KEY: CDS
<222> LOCATION: (1)...(369)
<223> OTHER INFORMATION: Heavy Chain V Region

<400> SEQUENCE: 25

```
caa gtt act ctt aag gag tct ggc cct ggg ata ttg aag ccc tca cag      48
Gln Val Thr Leu Lys Glu Ser Gly Pro Gly Ile Leu Lys Pro Ser Gln
  1               5                  10                  15 acc ctc agt ctg act tgt tct ttc tct ggg ttt tct ctg agc act tct      96
Thr Leu Ser Leu Thr Cys Ser Phe Ser Gly Phe Ser Leu Ser Thr Ser
                 20                  25                  30 ggt atg ggt att gcc tgg gtt cgt cag cct tca ggg aag ggt ctg gag     144
Gly Met Gly Ile Ala Trp Val Arg Gln Pro Ser Gly Lys Gly Leu Glu
             35                  40                  45 tgg ctg gca gac att tgg tgg gat gat aat aag tat tat aat cca tcc     192
Trp Leu Ala Asp Ile Trp Trp Asp Asp Asn Lys Tyr Tyr Asn Pro Ser
     50                  55                  60 ctg gag agc cag ctc aca atc tcc aag gat acc tcc aga aac cag gta     240
Leu Glu Ser Gln Leu Thr Ile Ser Lys Asp Thr Ser Arg Asn Gln Val
 65                  70                  75                  80 ttc ctc acg atc acc agt gtg gac act gca gat tct gcc act tat tac     288
Phe Leu Thr Ile Thr Ser Val Asp Thr Ala Asp Ser Ala Thr Tyr Tyr
                 85                  90                  95 tgt gct cgt cat cat tac gac ggt agt agc ctc ctg cct atg gac tac     336
Cys Ala Arg His His Tyr Asp Gly Ser Ser Leu Leu Pro Met Asp Tyr
                100                 105                 110 tgg ggt caa gga acc tca gtc acc gtc tcc tca                         369
Trp Gly Gln Gly Thr Ser Val Thr Val Ser Ser
            115                 120
```

<210> SEQ ID NO 26
<211> LENGTH: 123
<212> TYPE: PRT
<213> ORGANISM: Mus musculus

<400> SEQUENCE: 26

```
Gln Val Thr Leu Lys Glu Ser Gly Pro Gly Ile Leu Lys Pro Ser Gln
  1               5                  10                  15

Thr Leu Ser Leu Thr Cys Ser Phe Ser Gly Phe Ser Leu Ser Thr Ser
                 20                  25                  30

Gly Met Gly Ile Ala Trp Val Arg Gln Pro Ser Gly Lys Gly Leu Glu
             35                  40                  45

Trp Leu Ala Asp Ile Trp Trp Asp Asp Asn Lys Tyr Tyr Asn Pro Ser
     50                  55                  60

Leu Glu Ser Gln Leu Thr Ile Ser Lys Asp Thr Ser Arg Asn Gln Val
 65                  70                  75                  80

Phe Leu Thr Ile Thr Ser Val Asp Thr Ala Asp Ser Ala Thr Tyr Tyr
                 85                  90                  95

Cys Ala Arg His His Tyr Asp Gly Ser Ser Leu Leu Pro Met Asp Tyr
                100                 105                 110

Trp Gly Gln Gly Thr Ser Val Thr Val Ser Ser
            115                 120
```

<210> SEQ ID NO 27
<211> LENGTH: 21
<212> TYPE: DNA
<213> ORGANISM: Mus musculus
<220> FEATURE:
<221> NAME/KEY: CDS
<222> LOCATION: (1)...(21)
<223> OTHER INFORMATION: VH13G9 Heavy Chain CDR I

<400> SEQUENCE: 27

```
act tct ggt atg ggt att gcc                                    21
Thr Ser Gly Met Gly Ile Ala
 1               5
```

<210> SEQ ID NO 28
<211> LENGTH: 7
<212> TYPE: PRT
<213> ORGANISM: Mus musculus

<400> SEQUENCE: 28

```
Thr Ser Gly Met Gly Ile Ala
 1               5
```

<210> SEQ ID NO 29
<211> LENGTH: 48
<212> TYPE: DNA
<213> ORGANISM: Mus musculus
<220> FEATURE:
<221> NAME/KEY: CDS
<222> LOCATION: (1)...(48)
<223> OTHER INFORMATION: VH13G9 Heavy Chain CDR II

<400> SEQUENCE: 29

```
gac att tgg tgg gat gat aat aag tat tat aat cca tcc ctg gag agc    48
Asp Ile Trp Trp Asp Asp Asn Lys Tyr Tyr Asn Pro Ser Leu Glu Ser
 1               5                  10                  15
```

<210> SEQ ID NO 30
<211> LENGTH: 16
<212> TYPE: PRT
<213> ORGANISM: Mus musculus

<400> SEQUENCE: 30

```
Asp Ile Trp Trp Asp Asp Asn Lys Tyr Tyr Asn Pro Ser Leu Glu Ser
 1               5                  10                  15
```

<210> SEQ ID NO 31
<211> LENGTH: 39
<212> TYPE: DNA
<213> ORGANISM: Mus musculus
<220> FEATURE:
<221> NAME/KEY: CDS
<222> LOCATION: (1)...(39)
<223> OTHER INFORMATION: VH13G9 Heavy Chain CDR III

<400> SEQUENCE: 31

```
cat cat tac gac ggt agt agc ctc ctg cct atg gac tac               39
His His Tyr Asp Gly Ser Ser Leu Leu Pro Met Asp Tyr
 1               5                  10
```

<210> SEQ ID NO 32
<211> LENGTH: 13
<212> TYPE: PRT
<213> ORGANISM: Mus musculus

<400> SEQUENCE: 32

```
His His Tyr Asp Gly Ser Ser Leu Leu Pro Met Asp Tyr
 1               5                  10
```

<210> SEQ ID NO 33
<211> LENGTH: 324
<212> TYPE: DNA
<213> ORGANISM: Rattus norvegicus
<220> FEATURE:
<221> NAME/KEY: CDS
<222> LOCATION: (1)...(324)
<223> OTHER INFORMATION: Light Chain V Region

<400> SEQUENCE: 33

```
gat att caa atg acg cag tct cca gct tcc ctg tct gca tct ctg gga      48
Asp Ile Gln Met Thr Gln Ser Pro Ala Ser Leu Ser Ala Ser Leu Gly
 1               5                  10                  15 gaa act gtc tcc atc gaa tgt cta gca agt gag gac ata tac agt tat      96
Glu Thr Val Ser Ile Glu Cys Leu Ala Ser Glu Asp Ile Tyr Ser Tyr
             20                  25                  30 tta gca tgg tat caa cag aag cca ggg aaa tct cct cag ctc ctg atc     144
Leu Ala Trp Tyr Gln Gln Lys Pro Gly Lys Ser Pro Gln Leu Leu Ile
         35                  40                  45 tat gcc aca aaa agg ttg caa gat ggg gtc cca tca cgg ttc agt ggc     192
Tyr Ala Thr Lys Arg Leu Gln Asp Gly Val Pro Ser Arg Phe Ser Gly
     50                  55                  60 agt gga tct ggc aca cag tat tct ctc aaa ata agc gac atg caa cct     240
Ser Gly Ser Gly Thr Gln Tyr Ser Leu Lys Ile Ser Asp Met Gln Pro
 65                  70                  75                  80 gaa gat gaa ggg gat tat ttc tgt cta cag aat tcc aag ttt ccg gtc     288
Glu Asp Glu Gly Asp Tyr Phe Cys Leu Gln Asn Ser Lys Phe Pro Val
                 85                  90                  95 acg ttc ggt tct ggg acc aag ctg gag atc aaa cgg                     324
Thr Phe Gly Ser Gly Thr Lys Leu Glu Ile Lys Arg
            100                 105
```

<210> SEQ ID NO 34
<211> LENGTH: 108
<212> TYPE: PRT
<213> ORGANISM: Rattus norvegicus

<400> SEQUENCE: 34

```
Asp Ile Gln Met Thr Gln Ser Pro Ala Ser Leu Ser Ala Ser Leu Gly
 1               5                  10                  15

Glu Thr Val Ser Ile Glu Cys Leu Ala Ser Glu Asp Ile Tyr Ser Tyr
             20                  25                  30

Leu Ala Trp Tyr Gln Gln Lys Pro Gly Lys Ser Pro Gln Leu Leu Ile
         35                  40                  45

Tyr Ala Thr Lys Arg Leu Gln Asp Gly Val Pro Ser Arg Phe Ser Gly
     50                  55                  60

Ser Gly Ser Gly Thr Gln Tyr Ser Leu Lys Ile Ser Asp Met Gln Pro
 65                  70                  75                  80

Glu Asp Glu Gly Asp Tyr Phe Cys Leu Gln Asn Ser Lys Phe Pro Val
                 85                  90                  95

Thr Phe Gly Ser Gly Thr Lys Leu Glu Ile Lys Arg
            100                 105
```

<210> SEQ ID NO 35
<211> LENGTH: 33
<212> TYPE: DNA
<213> ORGANISM: Rattus norvegicus
<220> FEATURE:
<221> NAME/KEY: CDS
<222> LOCATION: (1)...(33)
<223> OTHER INFORMATION: VK14B7 Light Chain CDR I

```
<400> SEQUENCE: 35 cta gca agt gag gac ata tac agt tat tta gca                          33
Leu Ala Ser Glu Asp Ile Tyr Ser Tyr Leu Ala
 1               5                  10

<210> SEQ ID NO 36
<211> LENGTH: 11
<212> TYPE: PRT
<213> ORGANISM: Rattus norvegicus

<400> SEQUENCE: 36

Leu Ala Ser Glu Asp Ile Tyr Ser Tyr Leu Ala
 1               5                  10

<210> SEQ ID NO 37
<211> LENGTH: 21
<212> TYPE: DNA
<213> ORGANISM: Rattus norvegicus
<220> FEATURE:
<221> NAME/KEY: CDS
<222> LOCATION: (1)...(21)
<223> OTHER INFORMATION: VK14B7 Light Chain CDR II

<400> SEQUENCE: 37 gcc aca aaa agg ttg caa gat                                          21
Ala Thr Lys Arg Leu Gln Asp
 1               5

<210> SEQ ID NO 38
<211> LENGTH: 7
<212> TYPE: PRT
<213> ORGANISM: Rattus norvegicus

<400> SEQUENCE: 38

Ala Thr Lys Arg Leu Gln Asp
 1               5

<210> SEQ ID NO 39
<211> LENGTH: 27
<212> TYPE: DNA
<213> ORGANISM: Rattus norvegicus
<220> FEATURE:
<221> NAME/KEY: CDS
<222> LOCATION: (1)...(27)
<223> OTHER INFORMATION: VK14B7 Light Chain CDR III

<400> SEQUENCE: 39 cta cag aat tcc aag ttt ccg gtc acg                                  27
Leu Gln Asn Ser Lys Phe Pro Val Thr
 1               5

<210> SEQ ID NO 40
<211> LENGTH: 9
<212> TYPE: PRT
<213> ORGANISM: Rattus norvegicus

<400> SEQUENCE: 40

Leu Gln Asn Ser Lys Phe Pro Val Thr
 1               5

<210> SEQ ID NO 41
<211> LENGTH: 368
<212> TYPE: DNA
<213> ORGANISM: Rattus norvegicus
<220> FEATURE:
<221> NAME/KEY: CDS
```

<222> LOCATION: (1)...(368)
<223> OTHER INFORMATION: Heavy Chain V Region

<400> SEQUENCE: 41

| gag | gtt | cag | ctt | cag | cag | tct | ggg | gct | gag | ctt | gtg | aga | cct | ggg | acc | 48 |
|---|---|---|---|---|---|---|---|---|---|---|---|---|---|---|---|---|
| Glu | Val | Gln | Leu | Gln | Gln | Ser | Gly | Ala | Glu | Leu | Val | Arg | Pro | Gly | Thr | |
| 1 | | | | 5 | | | | | 10 | | | | | 15 | | |

| tct | gtg | aag | ttt | tct | tgc | aaa | gtt | tct | ggc | gat | acc | cct | aca | aca | tac | 96 |
|---|---|---|---|---|---|---|---|---|---|---|---|---|---|---|---|---|
| Ser | Val | Lys | Phe | Ser | Cys | Lys | Val | Ser | Gly | Asp | Thr | Pro | Thr | Thr | Tyr | |
| | | | 20 | | | | | 25 | | | | | 30 | | | |

| tac | gtg | cac | ttt | gtg | aga | caa | agg | cct | gga | cag | ggt | ctg | gaa | tgg | ata | 144 |
|---|---|---|---|---|---|---|---|---|---|---|---|---|---|---|---|---|
| Tyr | Val | His | Phe | Val | Arg | Gln | Arg | Pro | Gly | Gln | Gly | Leu | Glu | Trp | Ile | |
| | | 35 | | | | | 40 | | | | | 45 | | | | |

| gga | agg | att | gat | cct | gag | gat | act | agt | act | aaa | tat | gct | gag | aag | ttc | 192 |
|---|---|---|---|---|---|---|---|---|---|---|---|---|---|---|---|---|
| Gly | Arg | Ile | Asp | Pro | Glu | Asp | Thr | Ser | Thr | Lys | Tyr | Ala | Glu | Lys | Phe | |
| 50 | | | | | 55 | | | | | 60 | | | | | | |

| aga | aat | aag | gcg | aca | ttc | act | gca | gat | cca | tcc | tcc | aac | aca | gcc | tac | 240 |
|---|---|---|---|---|---|---|---|---|---|---|---|---|---|---|---|---|
| Arg | Asn | Lys | Ala | Thr | Phe | Thr | Ala | Asp | Pro | Ser | Ser | Asn | Thr | Ala | Tyr | |
| 65 | | | | 70 | | | | | 75 | | | | | 80 | | |

| cta | aac | ctc | agc | agc | ctg | acc | cct | gag | gac | act | gca | acc | tat | ttt | tgt | 288 |
|---|---|---|---|---|---|---|---|---|---|---|---|---|---|---|---|---|
| Leu | Asn | Leu | Ser | Ser | Leu | Thr | Pro | Glu | Asp | Thr | Ala | Thr | Tyr | Phe | Cys | |
| | | | | 85 | | | | | 90 | | | | | 95 | | |

| acc | ata | atg | cgg | tac | cat | agt | acc | tat | agg | gtc | tat | gtt | atg | gat | ttc | 336 |
|---|---|---|---|---|---|---|---|---|---|---|---|---|---|---|---|---|
| Thr | Ile | Met | Arg | Tyr | His | Ser | Thr | Tyr | Arg | Val | Tyr | Val | Met | Asp | Phe | |
| | | | 100 | | | | | 105 | | | | | 110 | | | |

| tgg | ggt | caa | gga | act | gca | gtc | act | gtc | tcc | tc | | | | | | 368 |
|---|---|---|---|---|---|---|---|---|---|---|---|---|---|---|---|---|
| Trp | Gly | Gln | Gly | Thr | Ala | Val | Thr | Val | Ser | | | | | | | |
| | | | 115 | | | | | 120 | | | | | | | | |

<210> SEQ ID NO 42
<211> LENGTH: 122
<212> TYPE: PRT
<213> ORGANISM: Rattus norvegicus

<400> SEQUENCE: 42

Glu Val Gln Leu Gln Gln Ser Gly Ala Glu Leu Val Arg Pro Gly Thr
1               5                   10                  15

Ser Val Lys Phe Ser Cys Lys Val Ser Gly Asp Thr Pro Thr Thr Tyr
            20                  25                  30

Tyr Val His Phe Val Arg Gln Arg Pro Gly Gln Gly Leu Glu Trp Ile
        35                  40                  45

Gly Arg Ile Asp Pro Glu Asp Thr Ser Thr Lys Tyr Ala Glu Lys Phe
50                  55                  60

Arg Asn Lys Ala Thr Phe Thr Ala Asp Pro Ser Ser Asn Thr Ala Tyr
65                  70                  75                  80

Leu Asn Leu Ser Ser Leu Thr Pro Glu Asp Thr Ala Thr Tyr Phe Cys
                85                  90                  95

Thr Ile Met Arg Tyr His Ser Thr Tyr Arg Val Tyr Val Met Asp Phe
            100                 105                 110

Trp Gly Gln Gly Thr Ala Val Thr Val Ser
        115                 120

<210> SEQ ID NO 43
<211> LENGTH: 15
<212> TYPE: DNA
<213> ORGANISM: Rattus norvegicus
<220> FEATURE:
<221> NAME/KEY: CDS
<222> LOCATION: (1)...(15)
<223> OTHER INFORMATION: VH14B7 Heavy Chain CDR I

```
<400> SEQUENCE: 43 aca tac tac gtg cac                                                    15
Thr Tyr Tyr Val His
 1               5

<210> SEQ ID NO 44
<211> LENGTH: 5
<212> TYPE: PRT
<213> ORGANISM: Rattus norvegicus

<400> SEQUENCE: 44

Thr Tyr Tyr Val His
 1               5

<210> SEQ ID NO 45
<211> LENGTH: 51
<212> TYPE: DNA
<213> ORGANISM: Rattus norvegicus
<220> FEATURE:
<221> NAME/KEY: CDS
<222> LOCATION: (1)...(51)
<223> OTHER INFORMATION: VH14B7 Heavy Chain CDR II

<400> SEQUENCE: 45 agg att gat cct gag gat act agt act aaa tat gct gag aag ttc aga      48
Arg Ile Asp Pro Glu Asp Thr Ser Thr Lys Tyr Ala Glu Lys Phe Arg
 1               5                  10                  15 aat                                                                    51
Asn

<210> SEQ ID NO 46
<211> LENGTH: 17
<212> TYPE: PRT
<213> ORGANISM: Rattus norvegicus

<400> SEQUENCE: 46

Arg Ile Asp Pro Glu Asp Thr Ser Thr Lys Tyr Ala Glu Lys Phe Arg
 1               5                  10                  15

Asn

<210> SEQ ID NO 47
<211> LENGTH: 42
<212> TYPE: DNA
<213> ORGANISM: Rattus norvegicus
<220> FEATURE:
<221> NAME/KEY: CDS
<222> LOCATION: (1)...(42)
<223> OTHER INFORMATION: VH14B7 Heavy Chain CDR III

<400> SEQUENCE: 47 atg cgg tac cat agt acc tat agg gtc tat gtt atg gat ttc              42
Met Arg Tyr His Ser Thr Tyr Arg Val Tyr Val Met Asp Phe
 1               5                  10

<210> SEQ ID NO 48
<211> LENGTH: 14
<212> TYPE: PRT
<213> ORGANISM: Rattus norvegicus

<400> SEQUENCE: 48

Met Arg Tyr His Ser Thr Tyr Arg Val Tyr Val Met Asp Phe
 1               5                  10
```